US008435546B2

(12) United States Patent
Schreiber et al.

(10) Patent No.: US 8,435,546 B2
(45) Date of Patent: May 7, 2013

(54) COSMETIC, DERMATOLOGICAL OR PHARMACEUTICAL PREPARATIONS OF LIPID/WAX MIXTURES CONTAINING GASES (75) Inventors: Jörg Schreiber, Hamburg (DE); Frank Teuber, Nordstadt (DE); Martin Sattler, Hamburg (DE)

(73) Assignee: Beiersdorf AG, Hamburg (DE)

( * ) Notice: Subject to any disclaimer, the term of this patent is extended or adjusted under 35 U.S.C. 154(b) by 1675 days.

(21) Appl. No.: 11/335,472

(22) Filed: Jan. 20, 2006

(65) Prior Publication Data

US 2006/0147390 A1    Jul. 6, 2006

Related U.S. Application Data (63) Continuation of application No. PCT/EP2004/008272, filed on Jul. 23, 2004.

(30) Foreign Application Priority Data

Jul. 23, 2003  (DE) .................................. 103 33 710

(51) Int. Cl.
    *A61K 8/00*      (2006.01)
(52) U.S. Cl.
    USPC ........................................................ 424/401
(58) Field of Classification Search .................. None
    See application file for complete search history.

(56) References Cited

U.S. PATENT DOCUMENTS

| 4,569,839 | A | * | 2/1986 | Grollier et al. ................... 424/74 |
| 4,726,942 | A | * | 2/1988 | Lang et al. ....................... 424/47 |
| 4,844,902 | A | * | 7/1989 | Grohe ........................... 424/449 |
| 4,921,694 | A |   | 5/1990 | Hoppe et al. |
| 5,238,698 | A |   | 8/1993 | Zumbé et al. |
| 5,286,475 | A | * | 2/1994 | Louvet et al. ................... 424/45 |
| 5,318,778 | A |   | 6/1994 | Schmucker et al. |
| 5,648,067 | A |   | 7/1997 | Dillenburg et al. |
| 5,679,361 | A |   | 10/1997 | Pradier et al. |
| 5,718,888 | A |   | 2/1998 | Klier et al. |
| 5,885,561 | A | * | 3/1999 | Flemming et al. .............. 424/62 |
| 5,885,564 | A |   | 3/1999 | Zastrow et al. |
| 5,886,561 | A | * | 3/1999 | Eitan et al. ..................... 327/408 |
| 5,955,091 | A |   | 9/1999 | Hansenne |
| 6,080,795 | A |   | 6/2000 | Pantini |
| 6,146,649 | A |   | 11/2000 | Hansenne |

(Continued)

FOREIGN PATENT DOCUMENTS

| DE | 2323353 | 11/1974 |
| DE | 3740186 | 1/1989 |

(Continued)

OTHER PUBLICATIONS

English Language Abstract of JP 56-79613.

(Continued)

*Primary Examiner* — Anand Desai
*Assistant Examiner* — Melissa Mercier
(74) *Attorney, Agent, or Firm* — Abel Law Group, LLP.

(57) ABSTRACT

A cosmetic, dermatological or pharmaceutical preparation comprising from 10% to 99% by weight of one or more lipids, from 1% to 90% by weight of one or more waxes and at least 20% by volume of one or more gases.

39 Claims, 1 Drawing Sheet

U.S. PATENT DOCUMENTS

| | | |
|---|---|---|
| 6,251,954 B1 | 6/2001 | Roulier et al. |
| 6,461,621 B1 | 10/2002 | Gagnebien et al. |
| 2001/0033826 A1 | 10/2001 | Roulier et al. |
| 2002/0122811 A1 | 9/2002 | Stein et al. |
| 2003/0007943 A1 | 1/2003 | Krause et al. |
| 2003/0211070 A1 | 11/2003 | Stein et al. |
| 2004/0076651 A1 | 4/2004 | Brocks et al. |
| 2004/0247531 A1 | 12/2004 | Riedel et al. |
| 2005/0074471 A1 | 4/2005 | Bleckmann et al. |
| 2005/0118127 A1 | 6/2005 | Krause et al. |

FOREIGN PATENT DOCUMENTS

| | | |
|---|---|---|
| DE | 3938140 | 8/1991 |
| DE | 4009347 | 9/1991 |
| DE | 4204321 | 8/1993 |
| DE | 4229707 | 3/1994 |
| DE | 4229737 | 3/1994 |
| DE | 4237081 | 5/1994 |
| DE | 4309372 | 9/1994 |
| DE | 4324219 | 1/1995 |
| DE | 4327679 | 2/1995 |
| DE | 10113048 | 9/2002 |
| DE | 10128468 | 12/2002 |
| DE | 10134597 | 2/2003 |
| DE | 10147820 | 4/2003 |
| EP | 0575070 | 12/1993 |
| EP | 0864317 | 9/1998 |
| EP | 1197201 | 4/2002 |
| FR | 2789397 | 8/2000 |
| GB | 459583 | 1/1937 |
| JP | 56-79613 | 6/1981 |
| JP | 5679613 * | 6/1981 |
| WO | 02/05754 | 1/2002 |
| WO | 02/41847 | 5/2002 |
| WO | 02/074258 | 9/2002 |
| WO | 2005/009403 | 2/2005 |

OTHER PUBLICATIONS

English Language Abstract of DE 2323353.
English Language Abstract of DE 10134597.
English Language Abstract of FR 2789397.
German Society for Fat Economic (*Fette, Seifen, Anstrichmittel*, 76 135 [1974]).
English Language Abstract of DE 4009347.
English Language Abstract of DE 4204321.
English Language Abstract of DE 4229707.
English Language Abstract of DE 4229737.
English Language Abstract of DE 4324219.

* cited by examiner

COSMETIC, DERMATOLOGICAL OR PHARMACEUTICAL PREPARATIONS OF LIPID/WAX MIXTURES CONTAINING GASES

CROSS-REFERENCE TO RELATED APPLICATIONS

The present application is a continuation of International Application No. PCT/EP2004/008272, filed Jul. 23, 2004, the entire disclosure whereof is expressly incorporated by reference herein, which claims priority of German Patent Application No. 103 33 710.5, filed Jul. 23, 2003.

BACKGROUND OF THE INVENTION

1. Field of the Invention

The present invention relates to cosmetic, dermatological or pharmaceutical preparations based on lipids and/or lipid/wax mixtures which contain a gas or a gas mixture.

As a particular embodiment, the present invention relates to cosmetic, dermatological or pharmaceutical preparations in the form of dispersed gas in lipid/wax mixtures, to methods for their preparation, and to their use for cosmetic, dermatological, pharmaceutical and medicinal purposes.

2. Discussion of Background Information

Gas-containing cosmetic preparations are known per se and have already been described in numerous patents. The gases used are, for example, oxygen, fluorinated gases, carbon dioxide, air, nitrogen and the like.

One way of stabilizing gases in cosmetic or dermatological preparations consists, for example, in preparing an O/W emulsion which is then supplied with gas. Such formulations are also known as mousse (for example WO 2002/074258 A1). A disadvantage of these prior art preparations is that the gas can only be stabilized through the use of emulsifiers. It is also disadvantageous that the gas can escape into the atmosphere during topical application or even during storage at 40° C. or above (for example in the car or on the beach). In addition, the loading capacity of such preparations is mostly rather low, meaning that physiological effects are not present following application.

Phospholipid-containing oxygen-laden fluorocarbon mixtures are also already known and have been described, for example, in DE 43 27 679 A1. These highly fluorinated mixtures are able to transport gases. A disadvantage, however, is the use of fluorinated compounds primarily because they represent xenophobic materials. A further disadvantage for a cosmetic, dermatological or pharmaceutical application is that phospholipids are expensive.

Hemoglobin or hemoglobin mixtures may also be oxygen carriers, as explained in WO 02/05754 A1. In addition, preparations are also known which comprise an oxygen precursor (hydrogen peroxide for example), which decomposes within the product and then releases the oxygen. A disadvantage of such preparations is that the oxygen can not be fixed very well within the product.

Gases—such as, for example, oxygen—can, in addition, also be subsequently introduced into an aerosol. The filling material of the aerosol consists then, for example, of a solution, an emulsion or an oil base. Following actuation of the valve, a foam is produced, the gas escaping into the atmosphere.

DE 101 28 468 A1 describes, moreover, a solid hair wax product which comprises at least one wax or a wax-like substance, these products having a largely homogeneous distribution of pores or gas bubbles in a solid wax matrix. The preparations can comprise up to 5% by weight of hydrophobic oils. In addition, these preparations also comprise emulsifiers, such as ethoxylated fatty alcohols, fatty acid ethoxylates, castor oil ethoxylates and ethoxylated phosphoric esters. These make it easier to wash out the preparations following application to the hair. The amount of emulsifiers is 3-20% by weight.

It would be advantageous to have available formulations which are characterized by a relatively high gas content. Desirable preparations should as far as possible be of cream-like (nonsolid) consistency and accordingly be suitable for cosmetic, dermatological or pharmaceutical applications.

SUMMARY OF THE INVENTION

The present invention provides a cosmetic, dermatological or pharmaceutical preparation which comprises (a) from 10% to 99% by weight, based on a total weight of the preparation, of one or more lipids, (b) from 1% to 90% by weight, based on a total weight of the preparation, of one or more waxes, and (c) at least 20% by volume, based on the total volume of the preparation, of one or more gases.

In one aspect, the preparation may comprise from 70% to 87% by weight of (a) and from 13% to 30% by weight of (b).

In another aspect, the preparation may further comprise from 0.1% to 10% by weight of one or more polyols such as, e.g., glycerol, propylene glycol, dipropylene glycol and butylene glycol. In another aspect, the one or more polyols may comprise up to 10% by weight of water.

In yet another aspect of the preparation of the present invention, component (b) may comprise one or more of beeswax, a paraffin wax, a triglyceride wax, a silicone wax and a polyethylene oxide wax. For example, component (b) may comprise micro-crystalline paraffin wax.

In a still further aspect of the preparation of the present invention, component (b) thereof may comprise one or more fatty acids. For example, component (b) may comprise stearic acid and/or behenic acid and/or fatty acid mixtures such as, e.g., $C_{16-36}$-fatty acid mixtures, and may further comprise a paraffin wax such as, e.g., microcrystalline wax.

In another aspect, the preparation of the present invention may comprise at least 13% by weight of stearic acid and, as oil, a paraffin oil and/or caprylic/capric triglyceride and/or cetearyl isononanoate and/or ethylhexyl cocoate and/or octyldodecanol.

In yet another aspect, component (b) of the preparation of the present invention may comprise one or more fatty alcohols such as, e.g., of behenyl alcohol, stearyl alcohol, cetearyl alcohol, cetylarachidol and 2-tetradecyloctadecanol, and may further comprise at least one of stearic acid, behenic acid, $C_{16-36}$-fatty acids and paraffin wax.

In a still further aspect, component (b) of the preparation may comprise behenic acid and behenyl alcohol and/or it may comprise stearic acid, stearyl alcohol and at least one further wax such as, e.g., a further oil component selected from butylene glycol dicaprylate/dicaprate, butyloctyl salicylate, hexadecyl benzoate, butyloctyl benzoate, C12-C15 alkyl benzoate, diisobutyl adipate, di(2-ethylhexyl) adipate, cocoglyceride, dicaprylyl ether and dicaprylyl carbonate.

In another aspect of the preparation of the present invention, component (a) thereof may comprise a mineral oil (paraffin oil) and/or cetearyl isononanoate and/or caprylic/capric triglyceride and/or ethylhexyl cocoate and/or octyldodecanol and/or a cyclic silicone oil and/or a linear silicone oil.

In yet another aspect, the preparation of the present invention may further comprise one or more fillers and/or one or more powder raw materials. By way of non-limiting example, these fillers and powder raw materials may be selected from one or more of starch, a starch derivative, boron nitride, Aerosils®, micropheres, bismuth oxychloride, titanized mica, silicon dioxide (fumed silica), spherical silicon dioxide beads, polymethyl methacrylate beads, micronized Teflon, an acrylate polymer, aluminum silicate, aluminum starch octenylsuccinate, bentonite, calcium silicate, cellulose, chalk, corn starch, glyceryl starch, hectorite, hydrated silica, kaolin, magnesium hydroxide, magnesium oxide, magnesium silicates, magnesium trisilicate, maltodextrin, montmorillonite, microcrystalline cellulose, rice starch, silica, talc, mica, titanium dioxide, zinc laurate, zinc myristate, zinc neodecanoate, zinc rosinate, zinc stearate, polyethylene, aluminum oxide, attapulgite, calcium carbonate, calcium silicate, dextran, kaolin, nylon, silica silylate, silk powder, serecite, tin oxide, titanium hydroxide, trimagnesium phosphate and walnut shell powder.

In a still further aspect, the preparation of the present invention may further comprise one or more dyes and/or one or more colored pigments and/or one or more pearlescent pigments and/or one or more effect pigments. By way of non-limiting example, the preparation may comprise one or more of a silicate pigment, talc, mica, sericite, ultramarine, an oxide of iron, titanium and/or zirconium, iron hydroxide, chromium hydroxide and Composite (titanium-treated mica).

In another aspect, the preparation of the present invention may further comprise a lipophilic UV protectant and/or a hydrophilic UV protectant.

In yet another aspect, component (b) of the preparation of the present invention may comprise a DAB wax and/or a DAC wax such as, e.g., one or more of wool wax alcohol, cetyl palmitate, beeswax, carnauba wax, cholesterol, cetyl alcohol, stearyl alcohol, cetearyl alcohol, stearic acid and paraffin wax.

In a still further aspect, component (a) of the preparation of the present invention may comprise a DAB oil and/or a DAC oil such as, e.g., one or more of petrolatum, paraffin oil, microcrystalline paraffin, a medium-chain triglyceride and an ester oil (for example, jojoba oil, isopropylpalmitate, octyldodecanol and/or castor oil).

In another aspect, component (c) of the preparation of the present invention may comprise one or more of air, oxygen, nitrogen, a nitrous oxide, a noble gas and carbon dioxide. Further, the preparation may comprise from 30% to 62% by volume of component (c).

In another aspect, the preparation of the present invention may be substantially anhydrous and/or substantially free of emulsifiers and/or substantially free of phospholipids.

The present invention also provides a cosmetic, dermatological or pharmaceutical preparation which comprises from 70% to 87% by weight, based on the total weight of the preparation, of one or more lipids, from 13% to 30% by weight, based on the total weight of the preparation, of one or more waxes, and at least 30% by volume, based on the total volume of the preparation, of one or more gases selected from air, oxygen, nitrogen, nitrous oxides, noble gases and carbon dioxide.

The present invention also provides a method of making the preparation of the present invention as set forth above, including the various aspects thereof. The method comprises, in a first step, melting a lipid/wax mixture, in a second step, introducing a gas or gas mixture into the lipid/wax mixture using a mixer and, in a third step, cooling the resultant preparation, thereby trapping the gas or gas mixture within the lipid/wax mixture. This method may further comprise a fourth step of mixing, with stirring, the preparation with an unsaturated oil.

The present invention also provides a bandage, mull, gauze or cloth, ointment, face mask and cosmetic product, all of which comprises the preparation of the present invention as set forth above, including the various aspects thereof.

The present invention also provides a method of treating diseased skin. The method comprises applying the preparation of the present invention as set forth above, including the various aspects thereof, to at least a part of the diseased skin. In one aspect of this method, skin cancer and/or psoriasis and/or seborrhea may be treated.

As set forth above, preparations according to the invention are obtainable, for example, by a method where
1) in a first step, a lipid/wax mixture is melted and
2) in a second step, a gas or gas mixture is introduced into the lipid/wax mixture using a mixer and
3) in a third step, the resulting preparation is cooled, resulting in inclusion of the gas within the lipid/wax system.

It is advantageous if shortly prior to introduction into the mixer or else within the mixer directly, a consistency-increasing viscosity is established (by lowering the temperature and through appropriate choice of the oil/wax mixture) so that the gas is introduced into a viscous oil/wax system.

Figure 1:
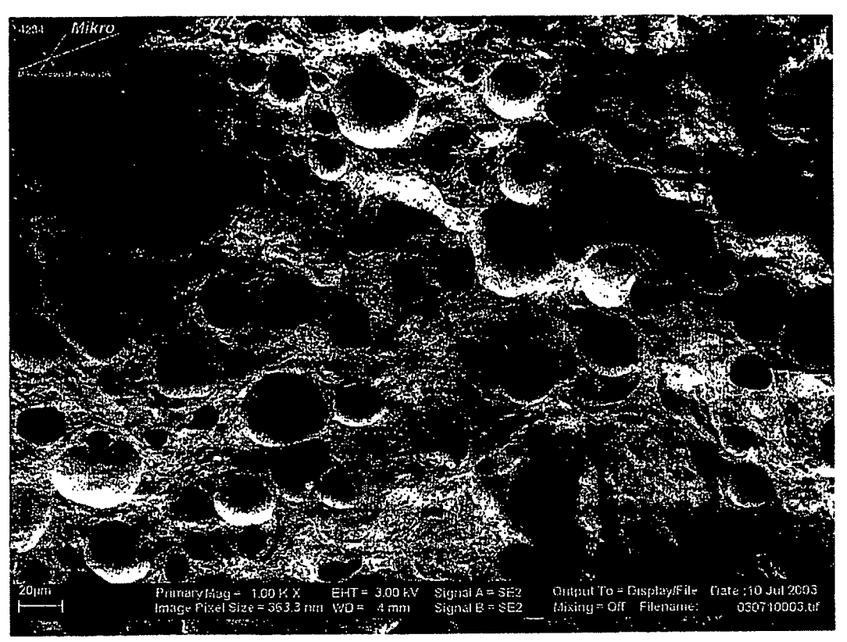

Surprisingly, it has been found that by the method according to the invention gas bubbles form in the lipid/wax system whose size is in the range from 0.5 µm to 50 µm (see FIG. 1). The size of the incorporated gas bubbles can be adjusted through the choice of the waxes and lipids and the settings on the mixer, temperature of the melt, cooling method of the melt.

In addition, in accordance with the invention it is possible—surprisingly without the addition of fluorinated or phospholipid-containing compounds and without the presence of emulsifiers—to stably incorporate very large amounts of gases (such as, for example, air, carbon dioxide or oxygen), it being possible to realize different gas introductions for one and the same preparation according to the invention, i.e. for example 10% by volume, 30% by volume, 50% by volume, 65% by volume oxygen introduction. Particularly advantageous preparations for the purposes of the present invention comprise between 30 and 62% by volume of gas, for example oxygen or air.

Although there is no general theory about this, it is assumed that upon cooling the warm gas/lipid/wax mixture, crystallization of the wax within the oil results, meaning that the gas can no longer escape and therefore a solid shell of wax or a solid shell of lipid/wax forms around the gas bubble. If the sensory properties of the mixture of the lipid/wax mixture are compared before and after introducing the gas, it can be found that the mixtures differ significantly. As expected, the first is oily or waxy, whereas the gas/lipid/wax system is more creamy. The introduction of gas thus has a positive influence on the texture, or even generates it for the first time. The numerous gas bubbles produce holes to a certain extent within the oil/wax system, meaning that, upon touching the system according to the invention, the formulation is more compressible compared to the pure lipid/wax system. This can also be established if a corresponding product is spread on the skin, which gives rise to pleasant sensory properties. The preparations according to the invention can therefore be referred to in a widest sense also as gas-in-lipid emulsions.

The formulations according to the invention are extraordinarily stable since the wax layer constitutes a good barrier for the gas. As is known, gases in water-based systems have a tendency for the larger bubbles to grow at the expense of the smaller bubbles, meaning that ultimately only large bubbles are present. In the present case, the gas bubbles are to a certain extent "frozen" in their place and are separated from one another by the rigid lipid/wax layer. A further advantage of the preparations according to the invention is that it is possible to stabilize relatively large concentrations of gas bubbles (similar to water in a water-in-oil emulsion), the gas (for example oxygen, carbon dioxide) only being released following application as a result of contact with the skin when the lipid/wax layer slowly dissolves. As a result of this, it is thus possible to transport larger amounts of gases onto the skin or into the skin than has previously been possible with preparations of the prior art.

Accordingly, the formulations according to the invention can be used for cosmetic, dermatological, pharmaceutical and medicinal purposes, for example for use in plasters, mull, gauze, cloths, face masks, as classic ointment, burn ointment, wound ointment. In addition, they can be used as bases for medicinal purposes, for treating diseased skin (e.g. for skin cancer, psoriasis, seborrhea, etc.).

In addition, active ingredients (hydrophilic, lipophilic, surface-active and/or combinations thereof) can also be advantageously incorporated into this novel administration system since here, in contrast to the pure oil/wax system, a new interface arises. Moreover, the incorporated gas acts to a certain extent as a diluting component for the lipid/wax system, meaning that the corresponding formulations are also less expensive (compared to purely oily bases).

According to the invention, it is advantageous to prepare phospholipid-free preparations. Also advantageous are anhydrous preparations (or those which comprise only a very small amount of water, which can be introduced, for example, by the raw materials used) and preparations which comprise no emulsifiers.

For the purposes of the present invention, it is also advantageous if the preparations comprise 0.1 to 10% by weight of one or more polyols, in particular 0.1 to 10% by weight of glycerol or corresponding concentrations of propylene glycol, dipropylene glycol, butylene glycol. For example, glycerol can be introduced in large concentrations (>0.2% by weight) without the formulations being sticky. It is assumed that the freedom from water of the administration system is responsible for this.

Since such glycerol/oil/wax formulations are homogeneous, the possibility is also opened up of using water-soluble or water-dispersible active ingredients which are pre-dissolved in the polyol and then mixed with the oil/wax system. It is also possible to introduce the active ingredient directly into the polyol-containing preparations according to the invention; said active ingredient then migrates by diffusion into the polar domains of the polyol(s). In particular active ingredients which are water-sensitive or oxygen-sensitive (or both) can be stabilized in this way. In this case, gases such as nitrogen, nitrous oxides, noble gases and/or carbon dioxide are useful.

Advantageous water-soluble active ingredients which can be incorporated into the preparations in the manner stated for the purposes of the present invention are:
  biotin.
  carnitine and derivatives
  creatine and derivatives
  folic acid
  pyridoxine
  niacinamide
  polyphenols (flavonoids such as, for example, alpha-glucosylrutin)
  ascorbic acid and derivatives
  hamamelis
  aloe vera
  panthenol
  Q-10
  amino acids.

In addition, according to the invention it is also advantageously possible to use water-containing glycerol (e.g. with 10% by weight of water) without the mixture becoming inhomogeneous.

The preparations according to the invention can, in addition, advantageously, although not mandatorily, also comprise cosmetic or pharmaceutical auxiliaries, additives and/or active ingredients.

It is generally known that oxygen can lead to the oxidation of lipids, particularly if unsaturated lipids are to be used, such as squalene, monoglycerides, diglycerides or triglycerides or else unsaturated waxes (cholesterol, wool wax, etc.). The corresponding peroxides can lead to skin incompatibilities. Since unsaturated lipids are often advantageous constituents of cosmetic preparations (castor oil is, for example, suitable for stabilizing acids such as salicylic acid), it is proposed according to the invention to prepare a preparation for the purposes of the present invention in the presence of saturated lipids and only then, i.e., following the introduction of gas, to add the unsaturated lipid. Since the oxygen is shielded from the unsaturated component by the saturated oil/wax system, the use of unsaturated components thus becomes possible.

In addition, according to the invention it is also possible to prepare preparations which comprise two or more gases in a lipid/wax system. In this way, two or more gases can be topically applied simultaneously. For the preparation, firstly gas/lipid/wax preparations each with a gas are prepared, which are then mixed in any desired ratios (advantageously from 9:1 to 1:9). For example, mixtures of oxygen/lipid/wax systems and carbon dioxide/lipid/wax systems in the ratios from 9:1 to 1:9 are advantageous.

In addition, to protect against oxidation, antioxidants can also advantageously be added to the preparations according to the invention. For the purposes of the present invention, it is also advantageous to add alcohols—such as, for example, ethanol—to the preparations according to the invention, for example if a cooling effect is to be achieved. In addition—particularly if a cooling effect is to be achieved—it is also possible to use substances such as menthol, camphor or the corresponding derivatives.

Lipids:

The lipid phase of the preparations according to the invention can advantageously be chosen from the group of branched and unbranched hydrocarbons, cyclic or linear silicone oils, siloxane elastomers, lanolins, adipic esters, butylene glycol diesters, dialkyl ethers or carbonates, the group of saturated or unsaturated, branched alcohols, and fatty acid triglycerides, namely the triglycerol esters of saturated and/or unsaturated, branched and/or unbranched alkanecarboxylic acids of chain lengths from 8 to 24, in particular 12-18, carbon atoms. The fatty acid triglycerides can, for example, advantageously be chosen from the group of synthetic, semisynthetic and natural oils, e.g. olive oil, sunflower oil, soya oil, peanut oil, rapeseed oil, almond oil, palm oil, evening primrose oil, coconut oil, palm kernel oil and the like.

The lipid component or the totality of the lipid components of the preparations according to the invention is preferably chosen from the group of esters of saturated and/or unsaturated, branched and/or unbranched alkanecarboxylic acids with a chain length of from 1 to 44 carbon atoms and saturated and/or unsaturated, branched and/or unbranched alcohols with a chain length of from 1 to 44 carbon atoms, from the group of esters of aromatic carboxylic acids and saturated and/or unsaturated, branched and/or unbranched alcohols with a chain length of from 1 to 30 carbon atoms if the lipid component or the totality of the lipid components constitute a liquid at room temperature. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, e.g. jojoba oil.

Ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, e.g. jojoba oil.

In addition, the lipid phase can advantageously have a content of cyclic or linear silicone oils or consist entirely of such oils, although it is preferred to use an additional content of other lipids apart from the silicone oil or the silicone oils.

Cyclomethicone (octamethylcyclotetrasiloxane) is advantageously used as silicone oil to be used according to the invention. However, other silicone oils are also to be used advantageously for the purposes of the present invention, for example hexamethylcyclotrisiloxane, polydimethylsiloxane, poly(methylphenylsiloxane).

Advantageous lipid components are also, for example, butyloctyl salicylate (for example the one available under the trade name Hallbrite BHB from CP Hall), hexadecyl benzoate and butyloctyl benzoate and mixtures thereof (Hallstar AB) and/or diethylhexyl naphthalate (Hallbrite TQ).

In addition, the lipids from Condea under the name cosmacols (cosmacol ETLP, ECL, ELI, EOI, EMI, ECI, ETI, ESI, EBI) can also be used advantageously (tartaric ester, citrate ester, lactate ester, octanoate ester, malate ester, salicylate and benzoate ester). For example, ETL (dialkyl tartrate) is a waxy component which can be used advantageously.

In addition, ethoxylated and/or propoxylated oils can also be used, such as PPG-14 butyl ether and the like.

Very particularly advantageous lipid components can be chosen from the group consisting of ethylhexyl cocoate, isotridecyl isononanoate, cetearyl isononanoate, myristyl myristate, dicaprylyl ether, distearyl ether, dicaprylyl carbonate, cetearyl isononanoate, octyldodecanol, polydecene, PPG-14 butyl ether, squalane, dicaprylyl ether, batyl alcohol, selachyl alcohol, triisostearin, butylene glycol dicaprylate/dicaprate, castor oil, caprylic/capric triglyceride, diisobutyl adipate, di(2-ethylhexyl) adipate, lanolin oil, isopropyl palmitate, cocoglyceride, cyclomethicone, dimethicone. In addition, natural oils, such as avocado oil, almond oil and macadamia oil are also particularly advantageous.

In addition, the lipids and oils for the purposes of the present invention may have DAB or DAC quality if dermatological or pharmaceutical applications are of prime importance (sunburn, plasters, mull, gauze, linen, covering films, skin cancer treatment, psoriasis, seborrhea, burn ointments, wound ointments).

Paraffin bases, for example, are known as DAB oil (Vaseline, paraffin oil, microcrystalline paraffin DAC). In addition, medium-chain triglycerides, ester oils, such as jojoba oil, isopropyl palmitate and also octyldodecanol, castor oil are also then to be used advantageously.

The lipid components (one or more compounds) can advantageously be present in a content of from 35 to 90% by weight, based on the total preparation, preferably about 70 to 87% by weight, particularly about 72 to 86% by weight, very particularly about 75 to 85% by weight.

Waxes:

According to the stipulation of the German Society for Fat Economic (*Fette, Seifen, Anstrichmittel*, 76 135 [1974]), for characterizing the term "wax", it is usually the mechanico-physical properties of the waxes, which are decisive for their use which are used whereas the particular chemical composition is not taken into consideration when determining the term.

"Wax" is—similarly to "resin"—a collective name for a series of natural or artificially obtained substances. For the purposes of the present invention, waxes are compounds which have the following properties: kneadable at 20° C., solid to friably hard, coarsely to finely crystalline, transparent to opaque, but not glassy, melting above 30° C. without decomposition, even slightly above the melting point of relatively low viscosity and non-thread-drawing, strongly temperature-dependent consistency and solubility and polishable under slight pressure. In borderline cases, if more than one of the abovementioned properties is not satisfied for a substance, it is not a wax within the meaning of this definition. Waxes differ from similar synthetic or natural products (e.g. resins, plastic masses, etc.) primarily by virtue of the fact that they usually convert to the molten, low-viscosity state between about 50 and 90° C., in exceptional cases also up to about 200° C., and are virtually free from ash-forming compounds.

Of advantage according to the invention are, for example, natural waxes of animal and vegetable origin, such as, for example beeswax, China wax, bumblebee wax and other insect waxes, in particular those specified below.

Beeswax, for example, is a secretion product from glands of honey bees which they use for building honeycombs. Yellow (Cera flava), brown or red so-called raw wax is obtainable, for example, by melting the combs freed from the honey by centrifuging, separating the melt from solid impurities and allowing the raw wax thus obtained to solidify. The raw wax can be bleached completely white (Cera alba) by treatment with oxidizing agents.

Beeswax consists of the readily alcohol-soluble cerine, a mixture of cerotinic acid $CH_3(CH_2)_{24}COOH$ and melissic acid $CH_3(CH_2)_{28}COOH$, and of an ester mixture called myricin consisting of about 70 esters of $C_{16}$- to $C_{36}$-acids and $C_{24}$- to $C_{36}$-alcohols. Essential constituents of beeswax are myricyl palmitate, myricyl cerotinate and paraffin.

Other insect waxes, such as, for example, bumblebee wax, shellac wax or China wax are also essentially mixtures of different esters. China wax, for example, is deposited or produced in China and Japan from the wax scale (*Coccus ceriferus*) living on the Chinese ash and the scale species *Ceroplastes ceriferus* and *Ericerus pela*. It is scraped from the trees and purified by remelting in boiling water. The main constituent of China wax is the cerotinic acid ester of ceryl alcohol.

Shellac wax is obtained from lac, the secretion of the female lac insects (*Kerria lacca*), which live in huge colonies (lac is derived from the Hindi word "Lakh" for 100 000) on trees and shrubs in southern Asia (India, Burma, South China). The shellac wax obtainable by solvent extraction comprises myricyl alcohol, melissic acid and other wax alcohols and acids or esters thereof as essential constituents.

Plant waxes are also advantageous for the purposes of the present invention. Those which can preferably be used are cuticular waxes of lower and higher plants, algae, lichens, mosses and fungi, such as, for example, candelilla wax, carnauba wax, Japan wax, esparto grass wax, cork wax, rice wax, sugar cane wax, fruit waxes, e.g. apple wax, flower waxes, leaf waxes from conifers, coffee wax, flax wax, sesame wax, jojoba oil and the like.

Fatty alcohols and fatty alcohol mixtures which are obtainable from plant waxes are also advantageous for the purposes of the present invention. Those which can preferably be used are cuticular waxes of lower and higher plants, algae, lichens, mosses and fungi, such as, for example, candelilla wax, carnauba wax, Japan wax, esparto grass wax, cork wax, rice wax, sugar cane wax, fruit waxes, e.g. apple wax, orange wax, lemon wax, grapefruit wax, berry wax, bayberry wax, flower waxes, leaf waxes from conifers, coffee wax, flax wax, sesame wax, jojoba oil and the like.

Candelilla waxes, for example, are brownish to yellowish brown, hard waxy masses which are soluble in lipophilic solvents. Candelilla wax comprises odd-numbered aliphatic hydrocarbons (about 42%), esters (about 39%), wax acids and wax alcohols. It can be obtained, for example, from the comminuted, fleshy leaves of a thornless spurge species (*Euphorbia cerifera*) by boiling with aqueous sulfuric acid.

Carnauba wax is a yellowish, greenish or dark-gray mass which can be obtained in various qualities, obtained by selection, from the leaves of the Brazilian fan palm *Copernicia prunifera* or carnauba palm (*Carnauba cerifera*) by, for example, brushing the wax dust from the withered fronds, melting it and filtering it and, after solidification, breaking it into pieces. Carnauba wax can be lightened by bleaching agents. It comprises usually about 85% of esters, in each case about 2-3% free wax acids (carnaubic, behenic, lignoceric, melissic and cerotinic acid), long-chain alcohols, diols and saturated hydrocarbons.

Japan wax (also: Japan tallow or Cera japonica) is colorless or yellowish, pure plant fat which can be obtained, for example, in Japan from the fruits of a tree-like sumac plant (*Rhus succedanea*) by boiling. The main constituents of Japan wax are glyceryl palmitate and esters of japanic acid (heneicosanedioic acid, $C_{21}H_{40}O_4$), phellogenic acid (docosanedioic acid, $C_{22}H_{42}O_4$) and tricosanedioic acid ($C_{23}H_{44}O_4$).

Esparto wax is obtained as a by-product in pulp and paper manufacture from the esparto grass (Graminaceae) indigenous to Mediterranean countries. It consists of about 15 to 17% of wax acids (e.g. cerotinic and melissic acid), of 20 to 22% of alcohols and hydrocarbons, and of 63 to 65% of esters.

Of particular advantage for the purposes of the present invention are, for example, the natural waxes obtainable under the trade names Permulgin 1550 and Permulgin 4002 from KOSTER KEUNEN and those obtainable under the trade names Schellack Wachs 7302 L and Candellila Wachs 2039 L from KAHL Wachsraffinerie.

Chemically modified waxes and synthetic waxes are also advantageous according to the invention. Preferred modified waxes are, for example, beeswax esters, in particular the alkyl beeswaxes obtainable under the trade names BW Ester BW 67, BW Ester BW 80 from KOSTER KEUNEN.

Preferred synthetic waxes are, for example, that obtainable under the trade name Beeswax component B 85 from SCHLICKUM, and silicone-based waxes, such as, for example, dialkoxydimethylpolysiloxanes, which are characterized by the following structure in which x is a number between 18 and 24. Behenoxy dimethicone, for which x from the above structural formula is 21 and which is obtainable under the trade name Abil® Wax 2440 from Th. Goldschmidt AG is particularly advantageous. Also preferred according to the invention is a silicone-based wax which is available under the trade name Siliconyl Beeswax or Siliconyl Candellia from KOSTER KEUNEN.

Further advantageous synthetic waxes are certain fatty acid mixtures, for example $C_{16-36}$-fatty acids, in particular those which are available under the trade name Syncrowax AW1C from Croda GmbH. Also to be used advantageously as waxes for the purposes of the present invention are fatty acids, in particular unbranched, saturated fatty acids with a chain length of from 16 to 36 carbon atoms. Particular preference is given to palmitic acid, stearic acid and behenic acid.

If one or more fatty acids (alone or in combination with further waxes) are used as wax for the purposes of the present invention, it is particularly preferred according to the invention to choose mineral oil (paraffin oil) and/or cetearyl isononanoate and/or caprylic/capric triglyceride and/or ethylhexyl cocoate as constituent of the lipid phase or as sole lipid component. In this case, it is possible to dispense with classic waxes (ester waxes, triglyceride waxes, microcrystalline waxes, silicone waxes, etc.). In this case, the fatty acid (for example stearic acid) acts as consistency-increasing component for the oil (for example paraffin oil), meaning that—similarly to the oil bases thickened with classic waxes—viscous oil/fatty acid mixtures are present which are then converted into the gas-in-(oil/fatty acid) system with the gas. In this case, it is advantageous for the purposes of the present invention to use about 13 to 17% by weight of fatty acids based on the total weight of the preparation (before introducing the gas).

In addition, it is also possible for the purposes of the present invention, to choose mixtures of fatty acids and one or more classic waxes. In this case, the fraction of free fatty acids can be reduced from, for example, 17% by weight; for example, a mixture of microcrystalline wax (9.1% by weight) with stearic acid (13.6% by weight) can be chosen. In this example, an oil mixture of octyldodecanol, dicaprylyl ether, isodecyl neopentanoate, for example has proven useful.

In a further advantageous embodiment, the fraction of waxes for the purposes of the present invention (fatty acids and/or classic waxes) is to be limited to 15% by weight of the total preparation (without gas). According to the invention, it may also be advantageous to also further reduce the fraction of waxes for the purposes of the present invention.

If one or more fatty alcohols (alone or in combination with further waxes) are used as wax for the purposes of the present invention, it is particularly preferred according to the invention to choose mineral oil (paraffin oil) constituent of the lipid phase or as the sole lipid component. In this case it is possible to dispense with classic waxes (ester waxes, triglyceride waxes, microcrystalline waxes, silicone waxes, etc.). In this case, the fatty alcohol (for example behenyl alcohol) acts as consistency-increasing component for the oil (for example paraffin oil), meaning that—similarly to the oil bases thickened with classic waxes—viscous oil/fatty alcohol mixtures are present which are then converted into the gas-in-(oil/fatty alcohol) system with the gas. In this case, it is advantageous for the purposes of the present invention to use about 15 to 17% by weight of fatty alcohol based on the total weight of the preparation (before introducing the gas).

In addition, it is also advantageous for the purposes of the present invention to choose mixtures of fatty alcohols and one or more classic waxes. In this case, the fraction of free fatty alcohols can be reduced from, for example, 15% by weight; for example, a mixture of microcrystalline wax and behenyl alcohol can be chosen.

In addition, it is also advantageous according to the invention to choose mixtures of fatty alcohols and one or more fatty acids as wax components for the purposes of the present invention. In this case, the fraction of free fatty alcohols can be reduced from, for example, 15% by weight; for example, a mixture of behenyl alcohol and behenic acid can be chosen.

In addition, it is also advantageous for the purposes of the present invention to choose mixtures of fatty alcohols and one or more fatty acids in the presence of a classic wax, for example a mixture of stearic acid, stearyl alcohol and microcrystalline wax can be chosen.

If beeswax is chosen as the sole wax, octyldodecanol is a preferred oil. It is also possible to undertake mixings of octyldodecanol with other oils using beeswax.

Also advantageous for the purposes of the present invention are ester waxes, the esters of saturated and/or unsaturated, branched and/or unbranched alkanecarboxylic acids of chain length from 1 to 80 carbon atoms and saturated and/or unsaturated, branched and/or unbranched alcohols of chain length from 1 to 80 carbon atoms, from the group of esters of aromatic carboxylic acids and saturated and/or unsaturated, branched and/or unbranched alcohols of chain length from 1 to 80 carbon atoms if the wax component or the totality of the wax components constitute a solid at room temperature.

Ester waxes which are chosen from the group listed below are particularly advantageous:

| Ester wax | Trade name | obtainable from |
|---|---|---|
| Myristyl myristate | Cetiol MM | Henkel KgaA |
| Cetyl palmitate | Cutina CP | Henkel KgaA |
| $C_{14-34}$ alkyl stearate | Kesterwachs K 76 H | KOSTER KEUNEN |
| $C_{20-40}$ dialkyl dimerate | Kesterwachs K 80 D | KOSTER KEUNEN |
| Ditetracosanyl dimerate | Kesterwachs K70D | KOSTER KEUNEN |
| $C_{16-38}$ alkyl hydroxystearoylstearate | Kesterwachs K80P | KOSTER KEUNEN |
| $C_{20-40}$ alkyl stearoylstearoylstearate | Kesterwachs K80P-VS | KOSTER KEUNEN |
| $C_{20-40}$ alkyl stearate | Kesterwachs K 82 | KOSTER KEUNEN |
| Hydroxystearyl hydroxystearate | Elfacos C26 | AKZO NOBEL |

Also advantageous are esters of glycol, in particular glycol esters of lignoceric acid (CH3(CH2)22COOH), of cerotinic acid (CH3(CH2)24COOH) and/or of montanic acid (CH3(CH2)26COOH). For the purposes of the present invention, glycol esters of montanic acid (CH3(CH2)26COOH) are very particularly advantageous. An advantageous glycol montanate is available, for example in a mixture with butylene glycol montanate, under the trade name Wax E Pharma from Clariant.

It is also advantageous to choose the wax components from the group of glycerides, in particular from the group of triglycerides. The glycerides and triglycerides listed below are particularly advantageous:

| Glyceride | Trade name | obtainable from |
|---|---|---|
| $C_{16-18}$ triglyceride | Cremeol HF-52-SPC | Aarhus Oliefabrik |
| Glyceryl hydroxystearate | Naturchem GMHS | Rahn |
| Hydrogenated cocoglyceride | Softisan 100 | Hüls AG |
| Caprylic/capric/isostearic/adipic triglyceride | Softisan 649 | Dynamit Nobel |
| $C_{18-36}$ triglyceride | Syncrowax HGLC | Croda GmbH |
| Glyceryl tribehenate | Syncrowax HRC | Croda GmbH |
| Glyceryl tri(12-hydroxystearate) | Thixcin R | Rheox/NRC |
| Hydrogenated castor oil | Cutina HR | Henkel KGaA |
| $C_{16-24}$ triglyceride | Cremeol HF-62-SPC | Aarhus Oliefabrik |

For the purposes of the present invention, particular preference is also given to shea butter, also called karite butter or galam butter (CAS No. 68920-03-6). Shea butter is the fat of the seeds or kernels of the plant Butyrospermum Parkii belonging to the family of the Sapotaceae, which consists of about 34 to 45% by weight of solid fatty acids (primarily stearic acid) and about 50 to 60% by weight of liquid fatty acids (primarily comprising oleic acid).

| Silicone waxes | Trade name | obtainable from |
|---|---|---|
| Alkylated silicone polyether copolymer | VelvesilTM 125 Silicone Copolymer | GE Electric |
| Polyether modified silicone wax | SF 1388 | GE Electric |
| Branched C16-18 alkyl modified silicone wax | SF1632 | GE Electric |
| C30-45 alkyl modified silicone wax | SF 1642 | GE Electric |
| Dialkoxydimethylpolysiloxane | | |
| Stearyl dimethicone | SilCare 41M65 | Clariant |
| | Abil Wax 9800 | Goldschmidt |
| Behenoxy dimethicones | Abil Wax 2440 | Goldschmidt |
| C24-C28 alkyl methicones | SilCare 41M50 | Clariant |
| | Abil Wax 9810 P | Goldschmidt |
| C30-C45 alkyl methicones | AMS-C30 Wax | Dow Corning |
| C20-C24 alkyl methicones | SilCare 41M40 | Clariant |
| Stearoxy dimethicones | Abil Wax 2434 | Goldschmidt |
| Cetyl dimethicones | Cetylsil W | Biosil |
| C24-C28 alkyl dimethicones | SilCare 41M80 | Clariant |
| C20-C40 alkyl dimethicones | SilCare 41M70 | Clariant |

According to the invention, the waxes are also preferably chosen from the group of saturated and/or unsaturated, branched and/or unbranched fatty alcohols having 14 to 40 carbon atoms, particular preference being given to behenyl alcohol ($C_{22}H_{45}OH$), stearyl alcohol, cetearyl alcohol [a mixture of cetyl alcohol ($C_{16}H_{33}OH$) and stearyl alcohol ($C_{18}H_{37}OH$)], cetylarachidol [2-hexadecyl-1-eicosanol ($C_{36}H_{73}OH$)] and/or 2-tetradecyloctadecanol ($C_{32}H_{65}OH$). Advantageous embodiments of the two last-mentioned fatty alcohols are available under the trade names Isofol 36 and Isofol 32 from Condea.

For the purposes of the present invention, sterols can also be used advantageously: these include, for example, cholesterol and its derivatives, such as, for example, esters. The sterol esters can be obtained, for example, from Nippon Fine Chemical. Advantageous sterol derivatives are C10-40 isoalkyl acid cholesterol ester, cholesterol nonanoate, cholesterol oleate, cholesterol macadamiate, cholesterol lanolate. In addition, lanosterols and sitosterols can also be used advantageously for the purposes of the present invention.

In addition, the waxes can also have DAB or DAC quality if dermatological or pharmaceutical applications are of primary importance (sunburn, plasters, mull, gauze, linen, covering films, skin cancer treatment, psoriasis, seborrhea, burn ointments, wound ointments).

As DAB wax, wool wax alcohols, cetyl palmitate, beeswax, carnauba wax, cholesterol, cetyl alcohol, stearyl alcohol, cetearyl alcohol, stearic acid are to be chosen advantageously.

It is particularly preferred for the purposes of the present invention if the wax component or the totality of the wax components is chosen from the group of esters of saturated branched alkanecarboxylic acids with a chain length of from 1 to 44 carbon atoms and saturated branched alcohols with a chain length of from 1 to 44 carbon atoms if the wax component or the totality of the wax components constitute a solid at room temperature,
of natural waxes (beeswax, wool wax, apple wax, etc.)
of diesters of polyols and C10-C80 fatty acids,
of triglyceride waxes,
of silicone waxes
of sterols and sterol derivatives (cholesterol esters, branched, unbranched),
paraffin waxes (microcrystalline paraffin),
polyethylene oxide waxes.

For the purposes of the present invention, beeswax, C18-C36 triglyceride wax, cetyl palmitate, wool wax, hydrogenated castor oil, paraffin wax, microcrystalline wax, silicone wax and/or apple wax, for example, are very particularly advantageous.

Very particularly advantageous waxes for the purposes of the present invention are also palmitic acid, stearic acid, behenic acid or mixtures of fatty acids with one or more classic waxes, such as, for example, stearic acid/microcrystalline wax.

For the purposes of the present invention, it is advantageous to use waxes with a melting point of >60° C., where the wax phase can, however, also comprise waxes with a melting point of <60° C. if at least one wax with a melting point >60° C. is present.

The wax components (one or more compounds) can advantageously be present in a content of from 13% to 30% by weight, based on the total preparation, preferably from 14% to 28% by weight, in particular from 15% to 25% by weight.

If stearic acid is to be used as the sole wax component, a concentration of at least 13% to 15% by weight is to be chosen. This concentration can be reduced if a second wax is added.

If behenyl alcohol or stearyl alcohol are to be used as the sole wax component, a concentration of at least 15% by weight is to be chosen. This concentration can be reduced if a second wax is added.

The preparations according to the invention can, in addition, also advantageously comprise substances which lower the melting point of the wax or waxes, for example specific lipids, powders, fillers, sorbitan tristearate.

In addition, it is preferred if in addition a content of one or more water-soluble and/or water-swellable polymers is present, in particular cellulose and/or starch derivatives etherified with alkyl groups, preferably β-glucans, xanthan gum, dextrans, hydroxy-methylcellulose, hydroxyethylcellulose and/or hydroxypropylcellulose, methoxy-PEG-22/dodecyl glycol copolymers, poloxamers, hydrophilic starch esterified with one or more n-octenyl succinate radicals.

The cosmetic or dermatological preparations according to the invention can also advantageously, although not obligatorily, comprise fillers. For the purposes of the present invention, fillers are substances which change the sensory feel of pure lipid and/or lipid/wax mixtures and which, for example, further improve the sensory and cosmetic properties of the formulations and, for example, bring about or enhance a velvety or silky feel on the skin.

Advantageous fillers for the purposes of the present invention are starch and starch derivatives (such as, for example, tapioca starch, distarch phosphate, aluminum or sodium starch octenylsuccinate and the like [e.g. Dry Flo Elite LL, BN, PC from National Starch]), pigments which have neither primarily UV filter effect nor coloring effect (such as, for example, boron nitride, etc.) and/or Aerosils® (CAS No. 7631-86-9).

The so-called microspheres (specific powders) are also fillers for the purposes of the present invention. Microspheres are available, for example, from Kobo on the basis of polymethyl methacrylate, polyethylene, ethylene/acrylate copolymer, nylon 12, polyurethane, silicone resin and silica. The feel on the skin of lipid preparations can be adjusted from soft, creamy, soft/wet, slippery to hard/dry depending on the choice of microspheres. It is assumed that when microspheres are used, small round spheres roll over the surface of the skin to a certain degree and thus bring about the interesting sensory properties.

In addition, corresponding microsphere complexes from Kobo can also advantageously be used as fillers. These are microspheres provided with isopropyltitanium triisostearate, which can also be further modified.

Advantageous fillers for the purposes of the present invention are also powder substances. The powder substances used are, for example, bismuth oxychloride, titanized mica, silicon dioxide (fumed silica), spherical silicon dioxide beads, polymethyl methacrylate beads, micronized Teflon, boron nitride, acrylate polymers, aluminum silicate, aluminum starch octenylsuccinate, bentonite, calcium silicate, cellulose, chalk, corn starch, glyceryl starch, hectorite, hydrated silica, kaolin, magnesium hydroxide, magnesium oxide, magnesium silicates, magnesium trisilicate, maltodextrin, montmorillonite, microcrystalline cellulose, rice starch, silica, talc, mica, titanium dioxide, zinc laurate, zinc myristate, zinc neodecanoate, zinc rosinate, zinc stearate, polyethylene, aluminum oxide, attapulgite, calcium carbonate, calcium silicate, dextran, kaolin, nylon, silica silylate, silk powder, serecite, tin oxide, titanium hydroxide, trimagnesium phosphate, walnut shell powder or any desired mixtures.

Advantageous fillers for the purposes of the present invention are also pigments. Pigments based on silicates (talc, mica, sericite, ultramarine), metal oxides (iron, titanium, zirconium), metal hydroxides (iron, chromium), composites (titanium-treated mica), fillers (starch, celluloses) and the like, for example, are advantageous.

In addition, the pigments can be modified, such as, for example, aminosilicone-treated pigments and/or treated with silane, methicone or dimethicone.

As already explained, it is a particular advantage of the preparations according to the invention that they can comprise very large amounts of gases without emulsifiers being necessary to stabilize the gases.

It may, however, be advantageous, although it is not obligatory, to add stabilizers to the preparations for the purposes of the present invention, for example if the gas bubbles or pigments, powders, active ingredients, etc. are to be distributed homogeneously.

According to the invention, the stabilizers are advantageously chosen from the group of substances of the general formula A''' and A'''' are identical or different hydrophobic organic radicals,
a is a number from 1 to 100, preferably 2 to 60,
X is a single bond or the group

$R_1$ and $R_2$, independently of one another, are chosen from the group consisting of H, methyl, but where both radicals are not methyl at the same time,
$R_3$ is chosen from the group consisting of H and branched and unbranched, saturated and unsaturated alkyl and acyl radicals having 1 to 20 carbon atoms.

The structural formula is not to be interpreted in such a way that through the index a all of the radicals $R_1$, $R_2$ and $R_3$ represented in the brackets each have to be identical within the entire molecule. Rather, these radicals within each of the a fragments can be chosen freely.

The radicals A''' and A'''' may be identical or different and are preferably chosen from the group where $R_8$ and $R_9$ may be identical or different and are chosen from the group of saturated and unsaturated alkyl and acyl radicals having 1 to 30 carbon atoms, p is a number from 1 to 20 and Y is a single bond or the group where $R_3$ is chosen from the group consisting of H and the branched and unbranched, saturated and unsaturated alkyl and acyl radicals having 1 to 30 carbon atoms.

A preferred stabilizer is the PEG45/dodecyl glycol copolymer, which has the structure It is supplied by Akzo Nobel Chemicals GmbH under the name ELFACOS® ST 9. However, the corresponding PEG-22/dodecyl glycol copolymer is also to be used advantageously.

In addition, the group A''' and A'''', independently of one another, may also be alkyl radicals or acyl radicals. It is also particularly advantageous to use the methoxy-PEG-22 dodecyl glycol copolymer as stabilizer. It is supplied by Akzo Nobel Chemicals GmbH under the name ELFACOS® E 200.

The stabilizer or the stabilizers are advantageously present in concentrations of 0.01-25% by weight, although it is possible and advantageous to keep the content of stabilizers low, for example up to 5% by weight, in each case based on the total weight of the composition.

It is particularly advantageous then to use one or more of the abovementioned stabilizers if preparations according to the invention are to comprise a high content of destabilizing substances.

The cosmetic and dermatological preparations according to the invention can also comprise dyes and/or colored pigments, particularly if they are in the form of decorative cosmetics. The dyes and colored pigments can be chosen from the corresponding positive list of the Cosmetics Directive or the EC list of cosmetic colorants. In most cases, they are identical to the dyes approved for foods.

Advantageous colored pigments are, for example, titanium dioxide, mica, iron oxides (e.g. $Fe_2O_3$, $FE_3O_4$, $FeO(OH)$) and/or tin oxide. Advantageous dyes are, for example, carmine, Prussian blue, chromium oxide green, ultramarine blue and/or manganese violet. It is particularly advantageous to choose the dyes and/or colored pigments from the *Rowe Colour Index, 3rd edition*, Society of Dyers and Colourists, Bradford, England, 1971.

The colored pigments which can be used may be organic or inorganic in origin, such as, for example, organic ones of the azo type, indigoids, triphenylmethane-like, anthraquinones, and xanthine dyes, which are known as D&C and FD&C blues, browns, greens, oranges, reds, yellows. Inorganic ones consist of insoluble salts of certified dyes, which are referred to as lakes or iron oxides.

If the formulations according to the invention are in the form of products which are applied to the face, it is advantageous to choose, as dye, one or more substances from the following group: 2,4-dihydroxyazobenzene, 1-(2'-chloro-4'-nitro-1'-phenylazo)-2-hydroxynaphthalene, Ceres Red, 2-(sulfo-1-naphthylazo)-1-naphthol-4-sulfonic acid, calcium salt of 2-hydroxy-1,2'-azonaphthalene-1'-sulfonic acid, calcium and barium salts of 1-(2-sulfo-4-methyl-1-phenylazo)-2-naphthylcarboxylic acid, calcium salt of 1-(2-sulfo-1-naphthylazo)-2-hydroxynaphthalene-3-carboxylic acid, aluminum salt of 1-(4-sulfo-1-phenylazo)-2-naphthol-6-sulfonic acid, aluminum salt of 1-(4-sulfo-1-naphthylazo)-2-naphthol-3,6-disulfonic acid, 1-(4-sulfo-1-naphthylazo)-2-naphthol-6,8-disulfonic acid, aluminum salt of 4-(4-sulfo-1-phenylazo)-1-(4-sulfophenyl)-5-hydroxypyrazolone-3-carboxylic acid, aluminum and zirconium salts of 4,5-dibromofluorescein, aluminum and zirconium salts of 2,4,5,7-tetrabromofluorescein, 3',4',5',6'-tetrachloro-2,4,5,7-tetrabromofluorescein and its aluminum salt, aluminum salt of 2,4,5,7-tetraiodofluorescein, aluminum salt of quinophthalonedisulfonic acid, aluminum salt of indigodisulfonic acid, red and black iron oxide (CIN: 77 491 (red) and 77 499 (black)), iron oxide hydrate (CIN: 77 492), manganese ammonium diphosphate and titanium dioxide.

Also advantageous are oil-soluble natural dyes, such as, for example, paprika extracts, β-carotene or cochenille.

Also advantageous for the purposes of the present invention are formulations with a content of pearlescent pigments. Preference is given in particular to the types of pearlescent pigments listed below:
natural pearlescent pigments, such as, for example
"pearl essence" (guanine/hypoxanthine mixed crystals from fish scales) and
"mother of pearl" (ground mussel shells)
monocrystalline pearlescent pigments, such as, for example, bismuth oxychloride (BiOCl)
layer-substrate pigments: e.g. mica/metal oxide.

Bases for pearlescent pigments are, for example, pulverulent pigments or castor oil dispersions of bismuth oxychloride and/or titanium dioxide, and bismuth oxychloride and/or titanium dioxide on mica. The luster pigment listed under the CIN 77163 is particularly advantageous, for example.

Also advantageous are, for example, the following types of pearlescent pigments based on mica/metal oxide:

| Group | Coating/layer thickness | Color |
|---|---|---|
| Silver-white pearlescent pigments | $TiO_2$: 40-60 nm | silver |
| Interference pigments | $TiO_2$: 60-80 nm | yellow |
| | $TiO_2$: 80-100 nm | red |
| | $TiO_2$: 100-140 nm | blue |
| | $TiO_2$: 120-160 nm | green |
| Color luster pigments | $Fe_2O_3$ | bronze |
| | $Fe_2O_3$ | copper |
| | $Fe_2O_3$ | red |
| | $Fe_2O_3$ | red-violet |
| | $Fe_2O_3$ | red-green |
| | $Fe_2O_3$ | black |
| Combination pigments | $TiO_2/Fe_2O_3$ | gold shades |
| | $TiO_2/Cr_2O_3$ | green |
| | $TiO_2$/Prussian blue | deep blue |
| | $TiO_2$/carmine | red |

Particular preference is given, for example, to the pearlescent pigments obtainable from Merck under the trade names Timiron, Colorona or Dichrona.

The list of specified pearlescent pigments is not of course intended to be limiting. Pearlescent pigments advantageous for the purposes of the present invention are obtainable by numerous methods known per se. For example, other substrates apart from mica can be coated with further metal oxides, such as, for example, silica and the like. $SiO_2$ particles coated with $TiO_2$ and $Fe_2O_3$ ("ronaspheres"), which are sold by Merck and are particularly suitable for the visual reduction of fine lines, are advantageous, for example.

Moreover, it may be advantageous to dispense entirely with a substrate such as mica. Particular preference is given to iron pearlescent pigments which are prepared without the use of mica. Such pigments are obtainable, for example, under the trade name Sicopearl Kupfer 1000 from BASF.

Also of particular advantage are, in addition, effect pigments which are obtainable under the trade name Metasomes Standard/Glitter in various colors (yellow, red, green, blue) from Flora Tech. The glitter particles are present here in mixtures with various auxiliaries and dyes (such as, for example, the dyes with the Colour Index (CI) numbers 19140, 77007, 77289, 77491).

The dyes and pigments may either be present individually or in a mixture, and can be mutually coated with one another, different coating thicknesses generally giving rise to different color effects. The total amount of dyes and color-imparting pigments is advantageously chosen from the range from, for example, 0.1% by weight to 30% by weight, preferably from 0.5 to 15% by weight, in particular from 1.0 to 10% by weight, in each case based on the total weight of the preparations.

For the purposes of the present invention, it is advantageous to choose the lipid or the lipids from the group consisting of dioctyl sebacate, dicapryl ether, dicaprylyl carbonate, dibutyl adipate, cococaprylate/caprate, caprylic/capric triglyceride, glycerol diisostearate, glycerol triisostearate, lanolin alcohol, lanolin oil, tridecyl neopentanoate, isotridecyl isononanoate, cetyl octanoate, castor oil, isodecyl oleate, propylene glycol dicaprylate/caprate, octyldodecanol, octyldodecylstearoyl stearate, diisostearoyltrimethylolpropanesiloxysilicate, cocoglycerides, di C14-15 alkyl tartrate, pentaerythrityl ester or silicone oils if the preparations are to comprise pigments and/or powder substances.

The preparations according to the present invention represent extremely satisfactory preparations in every respect which are not limited to a restricted choice of raw materials. Accordingly, they are very particularly suited for use as a base for preparation forms with diverse application purposes. They can accordingly comprise customary auxiliaries, additives and/or active ingredients and be used for cosmetic or dermatological photoprotection, and also for the treatment, care and cleansing of the skin and/or of the hair and as make-up product in decorative cosmetics.

According to their particular composition, cosmetic or dermatological compositions for the purposes of the present invention can, for example, be used as skin protection cream, cleansing milk, day or night cream, etc. In some cases, it is possible and advantageous to use the compositions according to the invention as a base for pharmaceutical formulations.

Just as emulsions of liquid and solid consistency are used as cosmetic cleansing lotions or cleansing creams, the preparations according to the invention can also constitute cleansing preparations, which can be used, for example, to remove make-up or as mild washing foam—possibly also for blemished skin. Cleansing preparations of this type can advantageously also be used as so-called "rinse off" preparations, which are rinsed off from the skin following application.

For use, the preparations according to the invention are applied to the skin and/or the hair in an adequate amount in the manner customary for cosmetic and/or dermatological products.

The preparations according to the invention can comprise cosmetic auxiliaries as are customarily used in such preparations, e.g. complexing agents, bactericides, perfumes, substances for preventing or increasing foaming, dyes, pigments which have a coloring effect, thickeners, moisturizing and/or humectant substances or other customary constituents of a cosmetic or dermatological formulation, such as alcohols, polyols, polymers, foam stabilizers, electrolytes, organic solvents or silicone derivatives.

A further advantage of the preparations according to the invention is that it is usually possible to dispense with preservatives, preservative aids and the like if the preparations do not comprise a water phase.

Particularly advantageous preparations are also obtained if antioxidants are used as additive or active ingredient. According to the invention, the preparations advantageously comprise one or more antioxidants. Antioxidants which are favorable but nevertheless optional which may be used are all antioxidants which are customary or suitable for cosmetic and/or dermatological applications.

For the purposes of the present invention, water-soluble antioxidants can particularly advantageously be used, such as, for example, vitamins, e.g. ascorbic acid and derivatives thereof.

Preferred antioxidants are also vitamin E and derivatives thereof, and vitamin A and derivatives thereof.

The amount of antioxidants (one or more compounds) in the preparations is preferably from 0.001% to 30% by weight, particularly preferably from 0.05% to 20% by weight, in particular from 0.1% to 10% by weight, based on the total weight of the preparation.

If vitamin E and/or derivatives thereof are the antioxidant or the antioxidants, it is advantageous to choose their particular concentrations from the range from 0.001% to 10% by weight, based on the total weight of the formulation.

If vitamin A or vitamin A derivatives, or carotenes or derivatives thereof are the antioxidant or the antioxidants, it is advantageous to choose their particular concentrations from the range from 0.001% to 10% by weight, based on the total weight of the formulation.

It is particularly advantageous if the cosmetic preparations according to the present invention comprise cosmetic or dermatological active ingredients, preferred active ingredients being antioxidants which can protect the skin against oxidative stress.

Further advantageous active ingredients for the purposes of the present invention are natural active ingredients and/or derivatives thereof, such as, for example, alpha-lipoic acid, phytoene, D-biotin, coenzyme Q10, alpha-glucosylrutin, carnitine, carnosine, natural and/or synthetic isoflavonoids, creatine, taurine and/or β-alanine, and 8-hexadecene-1,16-dicarboxylic acid (dioic acid, CAS number 20701-68-2; provisional INCI name Octadecenedioic acid).

Formulations according to the invention which comprise, for example, known antiwrinkle active ingredients, such as flavone glycosides (in particular α-glycosylrutin), coenzyme Q10, vitamin E and/or derivatives and the like are particularly advantageously suitable for the prophylaxis and treatment of cosmetic or dermatological changes in the skin, as arise, for example, during skin aging (such as, for example, dryness, roughness and formation of dryness wrinkles, itching, reduced refatting (e.g. after washing), visible vascular dilations (telangiectases, couperosis), sagging and formation of lines and wrinkles, local hyperpigmentations, hypopigmentations and incorrect pigmentations (e.g. age spots), increased susceptibility to mechanical stress (e.g. cracking) and the like). In addition, they are advantageously suitable for combating the appearance of dry or rough skin.

The preparations according to the present invention can, in addition, also advantageously comprise self-tanning substances, such as, for example, dihydroxyacetone and/or melanin derivatives in concentrations of from 1% by weight to 8% by weight, based on the total weight of the preparation.

In addition, the preparations according to the present invention can also advantageously comprise repellents for protection against flies, ticks and spiders and the like. For example, N,N-diethyl-3-methylbenzamide (trade name: Metadelphene, "DEET"), dimethyl phthalate (trade name: Palatinol M, DMP), and in particular ethyl 3-(N-n-butyl-N-acetylamino)propionate (available under the trade name Insekt Repellent® 3535 from Merck) are advantageous. The repellents can be used either individually or in combination.

Moisturizers is the term used to refer to substances or mixtures of substances which confer on cosmetic or dermatological preparations the property, following application or spreading on the surface of the skin, of reducing the moisture loss from the horny layer (also called transepidermal water loss (TEWL)) and/or of having a beneficial effect on the hydration of the horny layer.

Advantageous moisturizers for the purposes of the present invention are, for example, glycerol, lactic acid and/or lactates, in particular sodium lactate, butylene glycol, propylene glycol, biosaccharide gum-1, glycine soya, ethylhexyloxyglycerol, pyrrolidonecarboxylic acid and urea. In addition, it is particularly advantageous to use polymeric moisturizers from the group of polysaccharides which are soluble in water and/or swellable in water and/or gellable using water. Particularly advantageous are, for example, hyaluronic acid, chitosan and/or a fucose-rich polysaccharide, which is listed in the Chemical Abstracts under the registry number 178463-23-5 and is obtainable, for example, under the name Fucogel®1000 from SOLABIA S.A. Moisturizers can advantageously also be used as antiwrinkle active ingredients for the prophylaxis and treatment of cosmetic or dermatological changes in the skin, as arise, for example, during skin aging.

It is also advantageous for the purposes of the present invention to create cosmetic and dermatological preparations whose main purpose is not protection against sunlight but which nevertheless comprise a content of further UV protectants. Thus, for example, UV-A and/or UV-B filter substances are usually incorporated into day creams or makeup products. UV protectants, like antioxidants and, if desired, preservatives, also constitute effective protection of the preparations themselves against spoilage. Cosmetic and dermatological preparations which are in the form of a sunscreen are also favorable.

Accordingly, the preparations for the purposes of the present invention preferably comprise at least one further UV-A, UV-B and/or broadband filter substance. The formulations can, but do not necessarily, optionally also comprise one or more organic and/or inorganic pigments as UV filter substances.

Preferred inorganic pigments are metal oxides and/or other metal compounds which are sparingly soluble or insoluble in water, in particular oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and mixtures of such oxides, and also the sulfate of barium ($BaSO_4$).

For the purposes of the present invention, the pigments can advantageously also be used in the form of commercially available oily or aqueous predispersions. Dispersion auxiliaries and/or solubilization promoters may advantageously be added to these predispersions.

According to the invention, the pigments can advantageously be surface-treated ("coated"), the intention being, for example, to form and/or retain a hydrophilic, amphiphilic or hydrophobic character. This surface treatment can consist in providing the pigments with a thin hydrophilic and/or hydrophobic inorganic and/or organic layer by methods known per se. The various surface coatings may also comprise water for the purposes of the present invention.

Inorganic surface coatings for the purposes of the present invention can consist of aluminum oxide ($Al_2O_3$), aluminum hydroxide $Al(OH)_3$, or aluminum oxide hydrate (also: alumina, CAS No.: 1333-84-2), sodium hexametaphosphate ($(NaPO_3)_6$), sodium metaphosphate ($(NaPO_3)_n$), silicon dioxide ($SiO_2$) (also: silica, CAS No.: 7631-86-9), or iron oxide ($Fe_2O_3$). These inorganic surface coatings can occur on their own, in combination and/or in combination with organic coating materials.

Organic surface coatings for the purposes of the present invention can consist of vegetable or animal aluminum stearate, vegetable or animal stearic acid, lauric acid, dimethylpolysiloxane (also: dimethicone), methylpolysiloxane (methicone), simethicone (a mixture of dimethylpolysiloxane with an average chain length of from 200 to 350 dimethylsiloxane units and silica gel) or alginic acid. These organic surface coatings can occur on their own, in combination and/or in combination with inorganic coating materials.

Zinc oxide particles and predispersions of zinc oxide particles suitable according to the invention are available under the following trade names from the companies listed:

| Trade name | Coating | Manufacturer |
|---|---|---|
| Z-Cote HP1 | 2% dimethicone | BASF |
| Z-Cote | / | BASF |
| ZnO NDM | 5% dimethicone | H&R |

Suitable titanium dioxide particles and predispersions of titanium dioxide particles are available under the following trade names from the companies listed:

| Trade name | Coating | Manufacturer |
|---|---|---|
| MT-100TV | Aluminum hydroxide/stearic acid | Tayca Corporation |
| MT-100Z | Aluminum hydroxide/stearic acid | Tayca Corporation |
| Eusolex T-2000 | Alumina/simethicone | Merck KgaA |
| Titanium dioxide T805 (Uvinul TiO$_2$) | Octyltrimethylsilane | Degussa |

An advantageous organic pigment for the purposes of the present invention is 2,2'-methylenebis(6-(2H-benzotriazol-2-yl)-4-(1,1,3,3-tetramethylbutyl)phenol) [INCI: Bisoctyltriazole], which is available under the trade name Tinosorb® M from CIBA-Chemikalien GmbH.

Advantageous UV-A filter substances for the purposes of the present invention are dibenzoylmethane derivatives, in particular 4-(tert-butyl)-4'-methoxydibenzoylmethane (CAS No. 70356-09-1), which is sold by Givaudan under the name Parsol® 1789 and by Merck under the trade name Eusolexe 9020.

A further advantageous UV-A filter substance for the purposes of the present invention is hexyl 2-(4'-diethylamino-2'-hydroxybenzoyl)benzoate (also: aminobenzophenone), which is characterized by the chemical structural formula Advantageous further UV filter substances for the purposes of the present invention are sulfonated, water-soluble UV filters, such as, for example, phenylene-1,4-bis(2-benzimidazyl)-3,3'-5,5'-tetrasulfonic acid and its salts, particularly the corresponding sodium, potassium or triethanolammonium salts, in particular the phenylene-1,4-bis(2-benzimidazyl)-3,3'-5,5'-tetrasulfonic bis-sodium salt with the INCI name Bisimidazylate (CAS No.: 180898-37-7), which is available, for example, under the trade name Neo Heliopan AP from Haarmann & Reimer;

salts of 2-phenylbenzimidazole-5-sulfonic acid, such as its sodium, potassium or triethanolammonium salt, and the sulfonic acid itself with the INCI name Phenylbenzimidazole Sulfonic Acid (CAS No. 27503-81-7), which is available, for example, under the trade name Eusolex 232 from Merck or under Neo Heliopan Hydro from Haarmann & Reimer;

1,4-di(2-oxo-10-sulfo-3-bornylidenemethyl)benzene (also: 3,3'-(1,4-phenylene-dimethylene)bis(7,7-dimethyl-2-oxobicyclo[2.2.1]hept-1-ylmethanesulfonic acid) and salts thereof (particularly the corresponding 10-sulfato compounds, in particular the corresponding sodium, potassium or triethanolammonium salt), which is also referred to as benzene-1,4-di(2-oxo-3-bornylidenemethyl-10-sulfonic acid). Benzene-1,4-di(2-oxo-3-bornylidenemethyl-10-sulfonic acid) has the INCI name Terephthalidene Dicamphor Sulfonic Acid (CAS No.: 90457-82-2) and is available, for example, under the trade name Mexoryl SX from Chimex;

sulfonic acid derivatives of 3-benzylidenecamphor, such as, for example, 4-(2-oxo-3-bornylidenemethyl)benzenesulfonic acid, 2-methyl-5-(2-oxo-3-bornylidenemethyl)sulfonic acid and salts thereof.

For the purposes of the present invention, advantageous UV filter substances are also so-called broadband filters, i.e. filter substances which absorb both UV-A and UV-B radiation.

Advantageous broadband filters or UV-B filter substances are, for example, triazine derivatives, such as, for example, 2,4-bis{[4-(2-ethylhexyloxy)-2-hydroxy]phenyl}-6-(4-methoxyphenyl)-1,3,5-triazine (INCI: Aniso Triazine), which is available under the trade name Tinosorb® S from CIBA-Chemikalien GmbH;

dioctylbutylamidotriazone (INCI: Dioctylbutamidotriazone), which is available under the trade name UVA-SORB HEB from Sigma 3V;

tris(2-ethylhexyl)-4,4',4"-(1,3,5-triazine-2,4,6-triylimino)trisbenzoate, synonym: 2,4,6-tris[anilino(p-carbo-2'-ethyl-1'-hexyloxy)]-1,3,5-triazine (INCI: Octyl Triazone), which is sold by BASF Aktiengesellschaft under the trade name UVINUL® T 150.

For the purposes of the present invention, an advantageous broadband filter is 2,2'-methylenebis(6-(2H-benzotriazol-2-yl)-4-(1,1,3,3-tetramethylbutyl)phenol), which is available under the trade name Tinosorb® M from CIBA-Chemikalien GmbH.

An advantageous broadband filter for the purposes of the present invention is also 2-(2H-benzotriazol-2-yl)-4-methyl-6-[2-methyl-3-[1,3,3,3-tetramethyl-1-[(trimethylsilyl)oxy]disiloxanyl]propyl]phenol (CAS No.: 155633-54-8) with the INCI name Drometrizole Trisiloxane.

The UV filter substances may be oil-soluble or water-soluble.

Advantageous oil-soluble filter substances are, for example:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)-benzoate, amyl 4-(dimethylamino) benzoate;

2,4,6-trianilino(p-carbo-2'-ethyl-1'-hexyloxy)-1,3,5-triazine;

esters of benzalmalonic acid, preferably di(2-ethylhexyl) 4-methoxybenzal-malonate;

esters of cinnamic acid, preferably 2-ethylhexyl 4-methoxycinnamate, isopentyl 4-methoxycinnamate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone and UV filters bonded to polymers.

Advantageous water-soluble filter substances are, for example: sulfonic acid derivatives of 3-benzylidenecamphor, such as, for example, 4-(2-oxo-3-bornylidenemethyl)benzenesulfonic acid, 2-methyl-5-(2-oxo-3-bornylidenemethyl)-sulfonic acid and salts thereof.

A further photoprotective filter substance to be used advantageously according to the invention is ethylhexyl 2-cyano-3,3-diphenylacrylate (octocrylene), which is available from BASF under the name Uvinul® N 539.

The list of specified UV filters which can be used for the purposes of the present invention is not of course intended to be limiting.

The preparations according to the present invention advantageously comprise the substances which absorb UV radiation in the UV-A and/or UV-B region in a total amount of, for example, from 0.1% by weight to 30% by weight, preferably from 0.5% to 20% by weight, in particular from 1.0% to 15.0% by weight, in each case based on the total weight of the preparations, in order to provide cosmetic preparations which protect the hair and/or the skin from the entire range of ultraviolet radiation.

For the purposes of the present invention, the preparations may in addition also advantageously be in the form of antiperspirants and/or deodorants.

Antiperspirants and/or deodorants are supplied in various application forms which have greatly differing viscosities (from stick-like to thin-liquid) and accordingly differ greatly with regard to their composition.

Preferred antiperspirant active ingredients for the purposes of the present invention are aluminum salts, such as, for example, aluminum chloride, aluminum chlorohydrate, nitrate, sulfate, acetate, etc. Also advantageous according to the invention are zinc, magnesium and zirconium compounds.

For the purposes of the present invention, the partially neutralized aluminum hydroxychlorides and zirconium/aluminum mixed salts are particularly advantageous.

Further advantageous antiperspirant agents for the purposes of the present invention are, for example, quaternary ammonium compounds of the general structural formula and alkylpyridinium salts of the general structural formula in which $R^1$ and $R^2$, independently of one another, are methyl or ethyl groups, $R^3$ is chosen from the group of alkyl radicals having 1 to 18 carbon atoms, $R^4$ is chosen from the group which is formed from the alkyl radicals having 8 to 18 carbon atoms and the aralkyl radicals having 7 to 18 carbon atoms, and $R^5$ is chosen from the group of alkyl radicals having 10 to 18 carbon atoms.

$X^-$ is an inorganic or organic anion, for example a halide (e.g. chloride or bromide), also an inorganic oxo element anion (of these in particular sulfate, carbonate, phosphate, borate and aluminate), and an alkyl sulfate (in particular ethyl sulfate) or, for example, a lactate, acetate, benzoate, propionate, tartrate, citrate and others besides.

For the purposes of the present invention, preference is given to quaternary ammonium compounds in which the radicals $R^1$, $R^2$, $R^3$ and $R^4$ are purely aliphatic compounds and $X^-$ is not a halide.

According to the invention, preference is given to benzalkonium chloride (N-alkyl-N,N-dimethylbenzylammonium chloride), cetrimonium bromide (N-hexadecyl-N,N,N-trimethylammonium bromide), cetyltrimethylammonium bromide, mecetronium ethyl sulfate (N-hexadecyl-N-ethyl-N,N-dimethylammonium ethyl sulfate), N,N-didecyl-N,N-dimethylammonium chloride and/or N,N-dioctyl-N,N-dimethylammonium chloride. Substances are also advantageously chosen from the group of benzyltrialkylammonium chlorides or bromides, such as, for example, benzyldimethylstearylammonium chloride, as antiperspirant agents.

Antiperspirant agents preferred according to the invention are also lauryl- or cetyl-pyrimidinium chloride. Very particular preference is given to mecetronium ethyl sulfate.

According to the invention, the antiperspirant active ingredients can advantageously be present either individually or in a mixture.

Preparations according to the invention particularly advantageously comprise the antiperspirant active ingredient or ingredients according to the invention in concentrations of from 4 to 20% by weight, preferably 5 to 15% by weight, in each case based on the total weight of the preparation.

The preparations according to the invention can advantageously also comprise deodorizing substances, for example odor concealers, such as the customary perfume constituents, odor absorbers, for example the sheet silicates described in the patent laid-open specification DE-P 40 09 347, of these in particular montmorillonite, kaolinite, ilite, beidellite, nontronite, saponite, hectorite, bentonite, smectite, also, for example, zinc salts of ricinoleic acid. Antimicrobial agents are likewise suited to being incorporated into the preparations according to the invention. Advantageous substances are, for example, 2,4,4'-trichloro-2'-hydroxydiphenyl ether (irgasan), 1,6-di(4-chlorophenylbiguanido)hexane (chlorhexidine), 3,4,4'-trichlorocarbanilide, quaternary ammonium compounds, oil of cloves, mint oil, thyme oil, triethyl citrate, farnesol (3,7,11-trimethyl-2,6,10-dodecatrien-1-ol), and the active agents described in German patent applications DE 37 40 186, DE 39 38 140, DE 42 04 321, DE 42 29 707, DE 42 29 737, DE 42 37 081, DE 43 09 372, DE 43 24 219.

The preparations according to the invention can also comprise pharmaceutical active ingredients, such as chloramphenicol, gentamicin sulfate, nystatin, hydrocortisone, cortisone, PVP-iodine, silver and/or silver compounds, camphor, menthol, neomycin, tobramycin, erythromycin, oxytetracycline.

Preparation of the Mixtures:

The preparations according to the invention can advantageously be prepared by the clear melt method (dissolution of all constituents and bottling) or the cream melt method (the active ingredients are dispersed in the molten mass and it is cooled quickly). The cream melt method is preferred in the case of rapidly sedimenting substances.

The method for producing the preparations according to the invention usually consists of the following steps:

melting all of the constituents at a temperature which is significantly greater than the melting point of the wax constituents.

heat-treating the preparation to a temperature just above the melting point of the wax.

the flowable preparation is then foamed in a continuous process using a dynamic foam generator (e.g. Top Mix from Hansa-Industrie-Mixer). During this, a gas is continuously incorporated in a constant product stream using a nozzle. In a dynamic mixer, gas and product stream are then homogeneously mixed. The degree of introduced shear energy can be controlled by adjusting the rotational speed. During the foaming process, the preparation is cooled considerably (cooling medium temperature 0 to 20° C.), so that, upon leaving the foam generator, it reaches a temperature of from 20 to 35° C.

The consistency of the preparations is between flowable and butter-like depending on the temperature setting, conveyed amount, gas fraction and amount of wax used. The density of the preparations is between 0.3 and 0.9 g/ml, preferably between 0.4 and 0.6 g/ml, depending on the amount of gas introduced.

Gases

The gases used are preferably air, oxygen, nitrogen, nitrous oxides ($N_2O$), noble gases, carbon dioxide, or combinations of two or more of the specified gases.

The examples below are intended to illustrate the present invention without limiting it. The numerical values in the examples are percentages by weight, based on the total weight of the particular preparations.

DETAILED DESCRIPTION OF THE INVENTION

Example 1

|  | % by wt. |
| --- | --- |
| Beeswax | 20 |
| Octyldodecanol | 80 |

The mixture is melted and supplied with air in a Hansa mixer. 50% air was taken up by the viscous lipid melt.

Example 2

|  | % by wt. |
| --- | --- |
| Stearic acid | 17 |
| Paraffin oil | 80 |
| Glycerol | 3 |

The mixture is melted and supplied with oxygen in a Hansa mixer. 54% oxygen was taken up by the viscous lipid melt.

Example 3

|  | % by wt. |
| --- | --- |
| Octyldodecanol | 36.4 |
| Dicaprylyl ether | 18.2 |
| Isocetyl neopentanoate | 18.2 |
| Microcrystalline wax (microcrystalline paraffin) | 9.1 |
| Stearic acid | 13.6 |
| Glycerol | 4.5 |

The mixture is melted and supplied with oxygen in a Hansa mixer. 62% oxygen was taken up by the viscous lipid melt.

Example 4

|  | % by wt. |
| --- | --- |
| Stearic acid | 15 |
| Caprylic/capric triglyceride | 82 |
| Glycerol | 3 |

The mixture is melted and supplied with oxygen in a Hansa mixer. 32% oxygen was taken up by the viscous lipid melt.

Example 5

|  | % by wt. |
| --- | --- |
| Stearic acid | 15 |
| Ethylhexyl cocoate | 82 |
| Glycerol | 3 |

The mixture is melted and supplied with oxygen in a Hansa mixer. 38% oxygen was taken up by the viscous lipid melt.

Example 6

|  | % by wt. |
| --- | --- |
| Stearic acid | 15 |
| Octyldodecanol | 82 |
| Glycerol | 3 |

The mixture is melted and supplied with oxygen in a Hansa mixer. 32% oxygen was taken up by the viscous lipid melt.

Example 7

|  | % by wt. |
| --- | --- |
| Stearic acid | 13 |
| Cetearyl isononanoate | 75 |
| Microcrystalline wax | 9 |
| Glycerol | 3 |

The mixture is melted and supplied with oxygen in a Hansa mixer. 51% oxygen was taken up by the viscous lipid melt.

Example 8

|  | % by wt. |
| --- | --- |
| C18-C36 triglyceride | 15 |
| Paraffin oil | 87 |
| Glycerol | 3 |

The mixture is melted and supplied with air in a Hansa mixer. 20% air was taken up by the viscous lipid melt.

Example 9

|  | % by wt. |
| --- | --- |
| Stearyl alcohol | 15 |
| Paraffin oil | 75 |
| Glycerol | 5 |
| Microcrystalline wax | 5 |

The mixture is melted and supplied with oxygen in a Hansa mixer. 30% oxygen was taken up by the viscous lipid melt.

Example 10

|  | % by wt. |
| --- | --- |
| Behenyl alcohol | 15 |
| Paraffin oil | 80 |
| Glycerol | 5 |

The mixture is melted and supplied with oxygen in a Hansa mixer. 50% oxygen was taken up by the viscous lipid melt.

Example 11

|  | % by wt. |
| --- | --- |
| Stearic acid | 17 |
| Paraffin oil | 80 |
| Glycerol | 3 |

The mixture is melted and supplied with air in a Hansa mixer. 42% air was taken up by the viscous lipid melt.

Example 12

|  | % by wt. |
| --- | --- |
| Cetearyl isononanoate | 82 |
| Wax K 82 | 15 |
| Glycerol | 3 |

The mixture is melted and supplied with gas in a Hansa mixer.

Example 13

A gas-lipid/wax mixture is prepared in accordance with one of Examples 1 to 12 and then a natural oil (evening primrose oil) is added with stirring.

Examples 14 to 22

The evening primrose oil in Example 13 is replaced by olive oil, sunflower oil, soya oil, peanut oil, rapeseed oil, almond oil, palm oil, or palm kernel oil, respectively.

What is claimed is:

1. A cosmetic, dermatological or pharmaceutical preparation, wherein the preparation comprises
    (a) from 10% to 99% by weight, based on a total weight of the preparation, of one or more lipids which comprise at least one lipid selected from mineral oils, cetearyl isononanoate, caprylic/capric triglycerides, ethylhexyl cocoate, octyldodecanol, cyclic silicone oils, and linear silicone oils;
    (b) from 1% to 90% by weight, based on a total weight of the preparation, of one or more waxes comprising at least on wax selected from beeswax and other insect waxes, paraffin waxes, synthetic waxes, chemically modified natural waxes, triglyceride waxes, fatty acids, fatty alcohols, candelilla waxes, carnauba waxes, Japan wax, esparto grass wax, cork wax, rice wax, sugar cane wax, flower waxes, leaf waxes from conifers, coffee wax, flax wax, and sesame wax; and
    (c) at least 20% by volume, based on a total volume of the preparation, of one or more gases;
and wherein the preparation is obtained by a process which comprises
    (i) melting a mixture of (a) and (b);
    (ii) incorporating (c) into the melted mixture of (a) and (b) using a mixer; and
    (iii) cooling the mixture obtained in (ii) to thereby occlude (c) within the mixture of (a) and (b),
gas bubbles in the preparation having a size of from 0.5 μm to 50 μm.

2. The preparation of claim 1, wherein the preparation comprises from 70% to 87% by weight of (a) and from 13% to 30% by weight of (b).

3. The preparation of claim 1, wherein the preparation further comprises one or more polyols.

4. The preparation of claim 3, wherein the one or more polyols comprise at least one of glycerol, propylene glycol, dipropylene glycol, and butylene glycol.

5. The preparation of claim 4, wherein the preparation comprises from 0.1% to 10% by weight of the one or more polyols.

6. The preparation of claim 1, wherein (b) comprises at least one wax selected from beeswax, paraffin waxes, triglyceride waxes, silicone waxes and polyethylene oxide waxes.

7. The preparation of claim 1, wherein (b) comprises microcrystalline paraffin wax.

8. The preparation of claim 1, wherein (b) comprises one or more fatty acids.

9. The preparation of claim 8, wherein (b) comprises at least one of stearic acid, behenic acid and $C_{16-36}$-fatty acid mixtures.

10. The preparation of claim 9, wherein (b) further comprises a paraffin wax.

11. The preparation of claim 1, wherein the preparation comprises at least 13% by weight of stearic acid and, as oil, at least one of paraffin oil, caprylic/capric triglyceride, cetearyl isononanoate, ethylhexyl cocoate, and octyldodecanol.

12. The preparation of claim 1, wherein (b) comprises at least one fatty alcohol.

13. The preparation of claim 12, wherein the one or more waxes comprise at least one of behenyl alcohol, stearyl alcohol, cetearyl alcohol, cetylarachidol, and 2-tetradecyloctadecanol.

14. The preparation of claim 13, wherein (b) further comprises at least one of stearic acid, behenic acid, $C_{16-36}$-fatty acid mixtures, and paraffin wax.

15. The preparation of claim 1, wherein (b) comprises behenic acid and behenyl alcohol.

16. The preparation of claim 1, wherein (b) comprises stearic acid, stearyl alcohol and at least one further wax.

17. The preparation of claim 16, wherein the at least one further wax comprises one or more of butylene glycol dicaprylate/dicaprate, butyloctyl salicylate, hexadecyl benzoate, butyloctyl benzoate, C12-C15 alkyl benzoate, diisobutyl adipate, di(2-ethylhexyl) adipate, cocoglyceride, dicaprylyl ether, and dicaprylyl carbonate.

18. The preparation of claim 1, wherein (a) comprises at least one lipid selected from mineral oils, cetearyl isononanoate, caprylic/capric triglycerides, ethylhexyl cocoate, octyldodecanol, cyclic silicone oils, and linear silicone oils.

19. The preparation of claim 1, wherein the preparation further comprises at least one of a lipophilic UV protectant and a hydrophilic UV protectant.

20. The preparation of claim 2, wherein (b) comprises one or more of wool wax alcohol, cetyl palmitate, beeswax, carnauba wax, cholesterol, cetyl alcohol, stearyl alcohol, cetearyl alcohol, stearic acid, and paraffin wax.

21. The preparation of claim 1, wherein the preparation comprises at least one of petrolatum, paraffin oil, microcrystalline paraffin, a medium-chain triglyceride, and an ester oil.

22. The preparation of claim 1, wherein (c) comprises at least one of air, oxygen, nitrogen, a nitrous oxide, a noble gas, and carbon dioxide.

23. The preparation of claim 22, wherein the preparation comprises from 30% to 62% by volume of (c).

24. The preparation of claim 1, wherein the preparation is substantially anhydrous.

25. The preparation of claim 1, wherein the preparation is free of emulsifiers.

26. The preparation of claim 1, wherein the preparation is free of phospholipids.

27. The preparation of claim 1, wherein the preparation has a density of from 0.3 g/ml to 0.9 g/ml.

28. A cosmetic, dermatological or pharmaceutical preparation, wherein the preparation comprises
(a) from 10% to 99% by weight, based on a total weight of the preparation, of one or more lipids,
(b) from 1% to 90% by weight, based on a total weight of the preparation, of one or more waxes,
(c) at least 20% by volume, based on a total volume of the preparation, of one or more gases; and
(d) from 0.1% to 10% by weight, based on a total weight of the preparation, of one or more polyols which comprise at least one of glycerol, propylene glycol, dipropylene glycol, and butylene glycol;
and wherein the preparation is obtained by a process which comprises
(i) melting a mixture of (a) and (b);
(ii) incorporating (c) into the melted mixture of (a) and (b) using a mixer; and
(iii) cooling the mixture obtained in (ii) to thereby occlude (c) within the mixture of (a) and (b),
gas bubbles in the preparation having a size of from 0.5 μm to 50 μm.

29. The preparation of claim 28, wherein the one or more polyols comprise at least glycerol.

30. The preparation of claim 28, wherein the preparation is substantially anhydrous.

31. The preparation of claim 28, wherein the preparation comprises from 30% to 62% by volume of (c).

32. The preparation of claim 28, wherein the preparation is free of emulsifiers.

33. The preparation of claim 28, wherein the preparation is free of phospholipids.

34. The preparation of claim 28, wherein the preparation has a density of from 0.3 g/ml to 0.9 g/ml.

35. The preparation of claim 28, wherein the preparation is comprised in at least one of a bandage, a mull, a gauze, and a cloth.

36. The preparation of claim 28, wherein the preparation is present as one of a facemask and an ointment.

37. A cosmetic, dermatological or pharmaceutical preparation, wherein the preparation comprises
(a) from 10% to 99% by weight, based on a total weight of the preparation, of one or more lipids,
(b) from 1% to 90% by weight, based on a total weight of the preparation, of one or more waxes; and
(c) at least 20% by volume, based on a total volume of the preparation, of one or more gases;
and is obtained by a process which comprises
(i) melting a mixture of (a) and (b);
(ii) incorporating (c) into the melted mixture of (a) and (b) using a mixer; and
(iii) cooling the mixture obtained in (ii) to thereby occlude (c) within the mixture of (a) and (b),
gas bubbles in the preparation having a size of from 0.5 μm to 50 μm,
and wherein the preparation is comprised in at least one of a bandage, a mull, a gauze, and a cloth, or is present as one of a facemask and an ointment.

38. The preparation of claim 37, wherein the preparation further comprises one or more of glycerol, propylene glycol, dipropylene glycol, and butylene glycol.

39. The preparation of claim 38, wherein the preparation is substantially anhydrous.

* * * * *